United States Patent [19]

Bright

[11] 4,060,524

[45] Nov. 29, 1977

[54] 6-ACYLAMIDO-2,2-DIMETHYL-3-(PYRIMIDIN-4,6-DIONE-2-YL)PENAMS

[75] Inventor: Gene Michael Bright, Groton, Conn.

[73] Assignee: Pfizer Inc., New York, N.Y.

[21] Appl. No.: 751,280

[22] Filed: Dec. 16, 1976

Related U.S. Application Data

[62] Division of Ser. No. 669,508, March 23, 1976, Pat. No. 4,028,360.

[51] Int. Cl.$^2$ .................... A61K 31/43; C07D 499/46; C07D 499/60; C07D 499/68
[52] U.S. Cl. ..................... 260/256.5 R; 260/239.1; 424/251
[58] Field of Search .................... 260/256.5 R, 239.1, 260/239.1 TB

[56] References Cited

FOREIGN PATENT DOCUMENTS 821,163  4/1975  Belgium .................... 260/239.1

Primary Examiner—Alton D. Rollins
Assistant Examiner—Lisa Jones
Attorney, Agent, or Firm—Connolly and Hutz

[57] ABSTRACT

Antibacterial 6-acylamido-2,2-dimethyl-3-(pyrimidin-4,6-dione-2-yl)penams, intermediates therefor, including 6-amino-2,2-dimethyl-3-(pyrimidin-4,6-dione-2-yl)penam, and processes for their preparation.

5 Claims, No Drawings

6-ACYLAMIDO-2,2-DIMETHYL-3-(PYRIMIDIN-4,6-DIONE-2-YL)PENAMS

CROSS-REFERENCE TO RELATED APPLICATION

This application is a division of application Ser. No. 669,508 filed Mar. 23, 1976, now U.S. Pat. No. 4,028,360.

BACKGROUND OF THE INVENTION

1. Field of the Invention

This invention relates to a class of β-lactam antibiotics and intermediates therefor. More particularly, it relates to penicillins in which the C.3 position bears a pyrimidin-4,6-dione-2-yl group in place of the carboxy group, and to intermediates for such compounds.

2. Description of the Prior Art

The penicillins, a β-lactam class of antibiotics, consist of N-acyl derivatives of 6-amino-2,2-dimethylpenam-3-carboxylic acid. Since the physicochemical and biological properties of the penicillins are largely determined by the nature of the C.6 substituent, chemical modification of the substituents on the penam nucleus has, until recently, focused on the C.6 position.

Efforts to improve the therapeutic value of the penicillins have also led to chemical modification at the C.3 position. The 3-carboxy group has been converted to a number of other groups such as salts, anhydrides, carbamyl, esters, thioacid, hydroxymethyl, acid azide, isocyanate, carbamates, hydroxamic and nitrile [Khokhlov, et al., Doklady Akad. Sci. Nauk. S.S.S.R. 135, 874–8 (1960); C.A. 55, 1139F (1961)]. A summary of such modifications is presented by Hamilton-Miller, Chemotherapia, 12, 73–88 (1967).

In addition, the 3-carboxy group has been replaced by formyl [Gottstein et al., J. Org. Chem., 31, 1922 (1966)], acid chloride [Wolfe et al. Can. J. Chem., 46, 2549 (1968)], hydroxy [Heusler, Helv. Chim. Acta, 55, 388 (1972)]; Sheehan and Brandt, J. Amer. Chem. Soc., 87, 5468 (1965)], diazoketone [Kleiner, Khim. Geterotsikl. Soed. 1966, 702; Ramsey and Stoodley, J. Chem. Soc. (C) 1969 1319], carboxymethyl [Kleiner loc. cit.], chloroketones (3-COCH$_2$Cl) [Ramsey and Stoodley, Chem. Commun. 1970, 1517], and the N-sulfonylamides (3-CONHSO$_2$Me) [U.S. Pat. No. 3,641,000]. With trivial exceptions of salts, certain easily hydrolyzed esters, and thioacids, all of these changes result in greatly diminished antibacterial activity.

It was recently reported, Belgian Patent No. 821,163, granted Apr. 17, 1975, that penams in which the 3-carboxy group is replaced by a 5-tetrazolyl group are highly effective antibacterial agents. Further, Belgian Patent No. 821,952, granted March 3, 1975, describes a series of 6-[2-(pyrimidin-2,4-dione-1-yl)acetamido]-2,2-dimethylpenam-3-carboxylic acids as antibacterial agents useful against penicillinase resistant antibiotics.

SUMMARY OF THE INVENTION

There has now been found a novel class of β-lactam antibiotics having formula I:

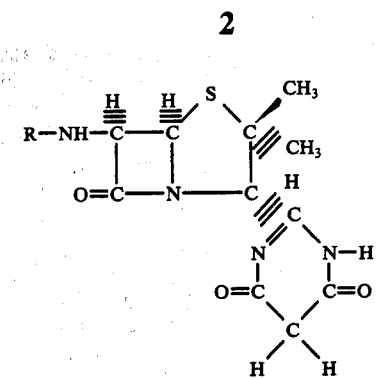

wherein R is selected from the group consisting of 2-phenylacetyl, 2-phenoxyacetyl, 2-azido-2-phenylacetyl and 2-amino-2-phenylacetyl which are effective against both Gram-positive and Gram-negative bacteria.

Also included in this invention are several compounds useful as intermediates for the preparation of compounds of formula I. The intermediates have formulae II and III:

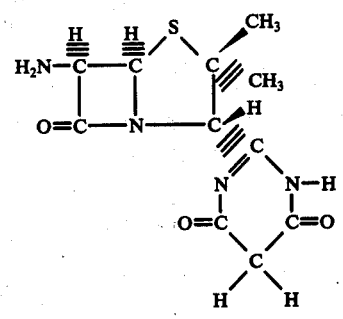

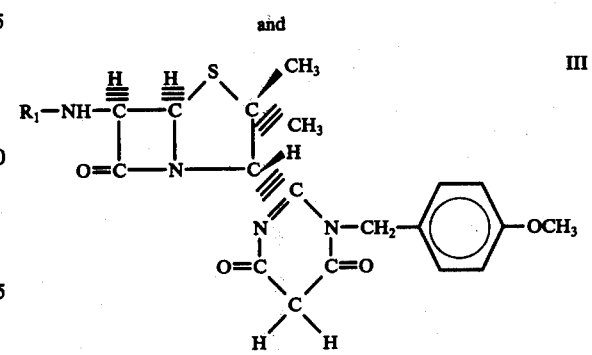

R$_1$, in formula III, is selected from the group consisting of hydrogen and

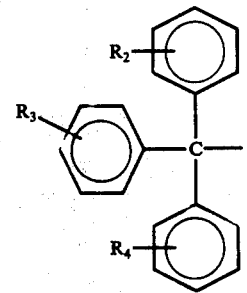

wherein each of R$_2$, R$_3$ and R$_4$ is selected from the group consisting of hydrogen, chloro, bromo, fluoro, alkyl having from one to four carbon atoms, alkoxy having from one to four carbon atoms, and phenyl.

Further, pharmaceutically-acceptable acid addition salts of compounds of formula II and of formula III wherein $R_1$ is hydrogen are also embraced with the scope of this invention. Representative acid addition salts are the hydrochloride, hydrobromide, sulfate, nitrate, acetate, propionate, butyrate, citrate, benzoate, malate, fumarate, maleate, gluconate, tartrate, glycolate, p-toluenesulfonate (tosylate), α- and β-naphthalenesulfonates, benzensulfonate, camphorsulfonate, glucoheptonate, lactate, methane sulfonate, hydroxynaphthoate and 7-aminonaphthalene-1,3-disulfonate.

For the sake of convenience, the compounds described herein are identified as derivatives of penam. The term "penam" has been defined in the *J. Am. Chem. Soc.*, 75, 3293 (1953), as referring to the structure:

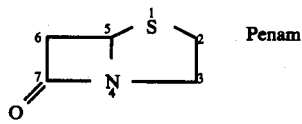 Penam

Using this terminology, the well-known antibiotic penicillin G is designated as 6-(2-phenylacetamido)-2,2-dimethyl-penam-3-carboxylic acid. The 3-(pyrimidin-4,6-dione-2-yl) surrogate of penicillin G, formula I above wherein R is 2-phenylacetyl, is designated as 6-(2-phenylacetamido)-2,2-dimethyl-3-(pyrimidin-4,6-2-yl)penam.

The 2-pyrimidin-4,6-diones, as is known, can exist in isomeric forms which, in solution at least, co-exist in a dynamic tautomeric, equilibrium mixture. Thus, in compounds of formulae I and II, the 2-pyrimidin-4,6-dione moiety can exist in various forms such as, for example:

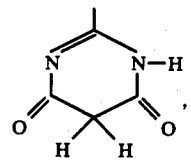

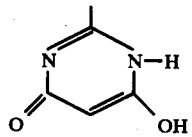

and

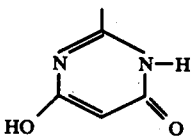

DETAILED DESCRIPTION OF THE INVENTION

The compounds of this invention are prepared according to the following reaction sequence wherein [P] represents the penam moiety; $R_O$ is triphenylmethyl or a substituted triphenylmethyl group as defined above under $R_1$, and TsO represents the tosylate anion. The $R_O$NH and COOH groups of the first formula of the sequence are located at the 6- and the 3-positions, respectively, of the penam structure.

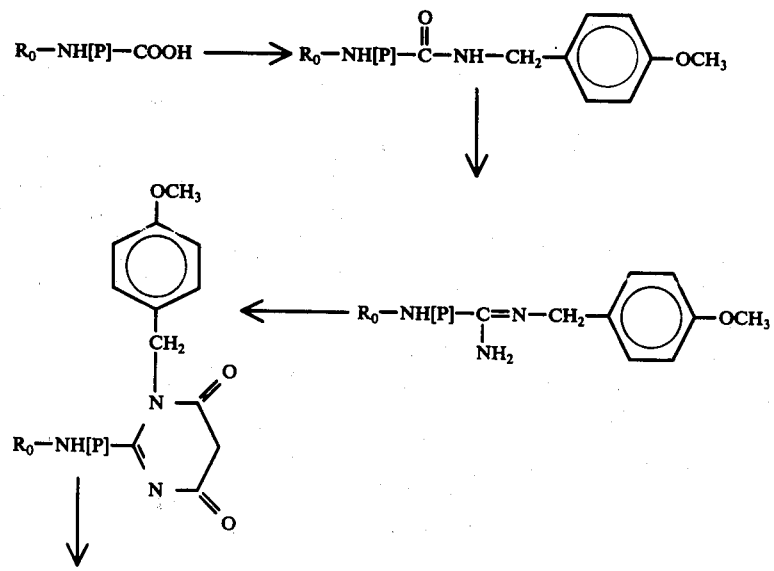

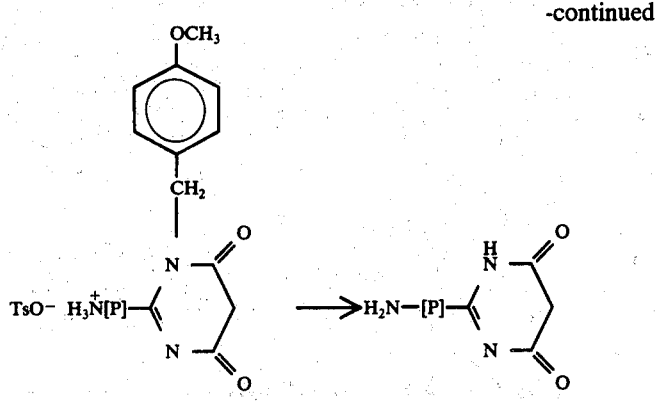

The process comprises converting 6-(triphenylmethylamino)penicillanic acid or a 6-(substituted-triphenylmethylamino)penicillanic acid to the corresponding N-(4-methoxybenzyl)carbamoyl derivative. Amide formation is conveniently achieved by means of the procedure described by Johnson, J. Am. Chem. Soc., 75, 3637-7 (1953). According to this procedure, the triethylammonium salt of the appropriate 6-(triphenylmethylamino)penicillanic acid is reacted with a lower alkyl chloroformate having from one to four carbon atoms in the alkyl group, e.g., ethyl chloroformate, in a reaction-inert solvent such as chloroform or methylene chloride to form a mixed anhydride. Alternatively, pivaloyl chloride can be used in place of a lower alkyl chloroformate. While the triethylammonium salt is, because of its solubility in the organic solvents normally used for the reaction, a favorite salt, other salts such as, alkali metal salts (sodium or potassium), and amine salts such as pyridinium, N-ethylpiperidinium or N,N-dimethylanilinium salts can be used. Reaction of the mixed anhydride with p-methoxybenzylamine is generally conducted by contacting the reactants in a reaction-inert solvent such as chloroform, methylene chloride, benzene, toluene, xylene, tetrahydrofuran, 1,2-dimethoxyethane or diethylether at a temperature of from about −30° C. to about 30° C. and preferably at about 0° C. The reactants are used in approximately equimolar proportions. The desired amide is isolated by standard procedures as, for example, by concentrating the organic solvent to dryness under reduced pressure to give the crude product. Alternatively, the reaction mixture is washed with water, the organic solution dried and concentrated to give the product, which is used as is.

The amide is then converted into an imido chloride by reaction with an appropriate halogenating agent such as thionyl chloride, a phosphorous halide such as phosphorous pentachloride, or phosgene in the presence of a base such as an organic amine (a tertiary amine such as triethylamine, N-methylmorpholine, pyridine, and trimethylamine). The reaction is generally conducted in a reaction-inert organic solvent at a temperature range from about −20° C. to about 30° C. The imido chloride is recovered by evaporation of the filtered reaction mixture.

The imido chloride is then transformed to an amidine by reaction in a reaction-inert solvent such as chloroform with ammonia. Amidine formation is achieved at temperatures from about −10° C. to about 30° C. and desirably at temperatures of from about 0° C. to about 25° C. The product is recovered by evaporation of the filtered reaction mixture. The amidine is then cyclized by reaction in a reaction-inert solvent medium with malonic acid in the presence of a condensing agent such as N,N'-dicyclohexylcarbodiimide. A variety of carbodiimides can, as those skilled in the art will recognize, be used in place of N,N'-dicyclohexylcarbodiimide. In this regard, reference is made to publications by Sheehan, et al., J. Org. Chem., 21, 439–441 (1956) and Khorana, Chem. Revs., 53, 154–7 (1953). Other dehydrative coupling agents can, of course, be used. Representative of such agents are N,N'-carbonyldiimidazole, N,N'-carbonyl-s-triazine, ethoxyacetylene and diphenylketene p-tolylamine. The 6-(triphenylmethylamino)-2,2-dimethyl-3-[1-(4-methoxybenzyl)-pyrimidine-4,6-dione-2-yl]penam is then treated with an acidic reagent in order to remove the protecting triphenylmethyl group from the 6-amino substituent.

The triphenylmethyl protecting group and substituted derivatives thereof are removed from compounds of formula III by treating the protected compound with a wide variety of acidic reagents under conditions known in the art for removal of a triphenylmethyl group. For example, it is possible to use a sulfonic acid, such as methanesulfonic acid, benzenesulfonic acid or p-toluenesulfonic acid; an anhydrous hydrohalic acid, such as hydrogen chloride or hydrogen bromide; or an alkanoic acid such as acetic acid, propionic acid, chloroacetic acid, trifluoroacetic acid and the like. The reaction is normally carried out by dissolving the starting material in an appropriate solvent and adding about two molar equivalents of the acid reagent at or about ambient temperature. Reaction is complete within about one hour, and the product is present in the reaction medium in the form of the acid-addition salt corresponding to the acidic reagent used. A solvent should be chosen which will dissolve the starting penam, and examples of solvents which find use are: ethers, such as diethyl ether, tetrahydrofuran, dioxane and 1,2-dimethoxyethane; chlorinated hydrocarbons, such as chloroform, methylene chloride and 1,2-dichloroethane; lower aliphatic ketones, such as acetone, methyl ethyl ketone and methyl isobutyl ketone; esters, such as ethyl acetate and butyl acetate; hydrocarbons, such as hexane, cyclohexane and benzene; and lower alkanols, such as methanol, ethanol and butanol. Although it is common to use about two molar equivalents of acid in this process, only one molar equivalent is necessary when the reaction is carried out in the presence of one molar equivalent of water, or the acid is introduced as a monohydrate. However, as will be realized by one skilled in the art, the product from this reaction should not be exposed to an excess of acid for prolonged periods, since in this case there is a danger of destroying the β-lactam system. A particularly convenient mode of operation for this process is to choose an acid-solvent system such that the starting material is soluble, but the acid addition salt generated during the reaction precipitates as it is formed. It can then be recovered by filtration at the end of the reaction. When using the combination of p-toluenesulfonic acid in acetone, the p-toluenesulfonate salt of the product often precipitates.

p-Toluenesulfonic acid is a favored reagent for removal of the triphenylmethyl or substituted triphenylmethyl protecting group on the 6-amino group. It permits recovery of the product in solid, frequently crystalline form.

The p-methoxybenzyl substituent is then removed from the 2-pyrimidinyl-4,6-dione moiety by treatment with anhydrous hydrogen fluoride. The reaction is conducted at a temperature of about −35° C. to about 0° C. and the product recovered, usually as a salt, by precipitation from the reaction mixture by addition of isopropyl ether.

Removal, or deblocking, of the triphenylmethyl substituent from the 6-amino group results in formation of an acid-addition salt corresponding to the acid reagent used for deblocking as noted above. The free base form of 6-amino-2,2-dimethyl-3-(pyrimidin-4,6-dione-2-yl)penam is conveniently obtained by neutralizing a solution of the acid-addition salt with an inorganic or organic base such as sodium or potassium hydroxide, triethylamine, or the hydroxide form of an anion exchange resin.

The 6-amino-2,2-dimethyl-3-(pyrimidin-4,6-dione-2-yl)penam is a valuable intermediate for the production of antibacterial agents of significant activity. Such compounds are prepared by acylation of 6-amino-2,2-dimethyl-3-(pyrimidin-4,6-dione-2-yl)penam (6-APP) with an activated derivative of the appropriate carboxylic acid, in an appropriate solvent system. An activated derivative commonly used is an acid halide, such as an acid chloride. In a typical acylation procedure, approximately one molar equivalent of an acid chloride is added to a solution of 6-APP, or a salt thereof, dissolved in a solvent such as chlorinated hydrocarbon, for example, chloroform or methylene chloride; an ether, for example, tetrahydrofuran or 1,2-dimethoxyethane; an ester, for example, ethyl acetate or butyl acetate; a lower aliphatic ketone, for example, acetone or methyl ethyl ketone or a tertiary amide, for example, N,N-dimethylformamide or N-methylpyrrolidone, at a temperature in the ranges from about −40° C. to about 30° C., and preferably from about −10° C. to about 10° C., optionally in the presence of about one molar equivalent of an acid-binder, e.g., triethylamine, pyridine or sodium bicarbonate. The reaction is complete within a short period, i.e., approximately one hour, and the product is isolated by techniques well known in the art, having full regard for the sensitive nature of the β-lactam moiety of the product. For example, the reaction mixture is evaporated to dryness and a water-immiscible organic solvent and water are added. In those cases where the product precipitates, it is filtered off. If the product does not precipitate, then the pH of the aqueous phase is adjusted to an appropriate value and the phase containing the product is evaporated. The crude product thus obtained can be purified further if desired. An alternate procedure useful for acylation with acid halides involves the use of an aqueous solvent system. In this procedure, which approximates the Schotten-Baumann procedure, the acid halide is added to a solution of the starting material in water, or a mixture of water and another inert solvent, being maintained within the pH range from about 6.0 to about 9.0 before, during, and after the addition. At the end of the reaction, the product can often be induced to precipitate by adjustment of the pH. Alternatively, it can be extracted into a water-immiscible solvent, which is then evaporated to dryness.

Another activated derivative of the carboxylic acid useful as an acylating agent is a mixed anhydride. In this procedure a solution of the preformed mixed anhydride is reacted with 6-APP, usually as a tertiary amine salt, for example, the triethylamine salt at a temperature in the range from about −30° C. to about 20° C., and preferably at about −10° C. In most instances the mixed anhydride and the 6-APP are contacted substantially in a 1:1 molar ratio. The product is usually isolated by evaporating the reaction mixture to dryness, and then adding a water-immiscible organic solvent and water. By careful adjustment of the pH, the product sometimes precipitates. In other cases the phases are separated, and the product-containing phase is evaporated to dryness. The crude product so obtained can be purified further if desired.

Another variation comprises conversion of the carboxylic acid to an active ester, followed by treatment with 6-APP or a salt thereof. Active esters which can be used are, for example, phenyl esters, such as p-nitrophenyl and 2,4,5-trichlorophenyl esters, thiol esters, such as thiolphenyl and thiolmethyl esters; and N-hydroxy esters, such as N-hydroxysuccinimide and N-hydroxyphthalimide esters. The esters are prepared by methods well established in the art, and the acylation is conveniently conducted by dissolving the active ester and the 6-APP or a salt thereof in a dipolar aprotic solvent such as N,N-dimethylformamide, N,N-dimethylacetamide or N-methylpyrrolidone. The solution is stored at about ambient temperature for several hours, for example overnight, and then the product is isolated by standard methods. In some instances the product can be isolated very simply by causing it to precipitate by the addition of a non-solvent, such as diethyl ether or acetone. It is then filtered off, and it can be purified, if desired, further. In many cases the active ester used in this process can be replaced by the corresponding acid azide.

A still further variation comprises contacting 6-APP with a carboxylic acid in the presence of certain agents known in the art for forming peptide bonds. Such agents include carbodiimides, for example, dicyclohexylcarbodiimide and 1-ethyl-3-(3-dimethylaminopropyl)-carbodiimide, alkoxyacetylenes, for example, methoxyacetylene and ethoxyacetylene, and N-ethoxycarbonyl-2-ethoxy-1,2-dihydroquinoline. The reaction is carried out in an appropriate solvent, i.e., one which will serve to dissolve the reactants, and does not adversely interact with the starting materials or the product, for example, acetonitrile, N,N-dimethylformamide and N-methylpyrrolidone.

The novel penicillins described herein exhibit in vitro activity against a wide variety of both gram-positive and gram-negative bacteria. Their useful activity can readily be demonstrated by in vitro tests against various organisms in a brain-heart infusion medium by the usual two-fold serial dilution technique. The in vitro activity of the herein-described compounds renders them useful for topical application in the form of ointments, creams and the like, or for sterilization purposes, e.g., sickroom utensils. For topical application, the dosage level is on the order of from about 10 to 200 mg./kg./day.

The in vitro (MIC) values for 6-(phenylacetamido)-2,2-dimethyl-3-(pyrimidin-4,6-dione-2-yl)penam against several organisms is presented below:

| Organism | MIC (μg./ml.) |
|---|---|
| Staphylococcus aureus 01AA005 | 50 |
| Staphylococcus aureus 01A099 | 50 |
| Streptococcus pyogenes 02C203 | 3.12 |
| Pasteurella multocida 59A001 | 50 |

When used for sterilization purposes, the compounds of this invention are used in solution or suspension at concentrations at least equal to the above MIC values. In actual practice, however, they are used at concentrations from 2-10 fold the MIC values.

When used for the purposes described herein, the valuable products of this invention can be used alone or in admixture with other antibiotics or in combination with a pharmaceutical carrier selected on the basis of the chosen route of administration and standard pharmaceutical practice. They may be injected parenterally; that is, for example, intramuscularly or subcutaneously. For parenteral administration they are best used in the form of a sterile solution or suspension which may be either aqueous such as water, isotonic saline, isotonic dextrose, Ringer's solution, or non-aqueous such as fatty oils of vegetable origin (cotton seed, peanut oil, corn, sesame) and other non-aqueous vehicles which will not interfere with the therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, as well as local anesthetics and inorganic salts to afford desirable pharmacological properties.

EXAMPLE 1

6-(Triphenylmethylamino)-2,2-dimethyl-3-[N-(4-methoxybenzyl)carbamoyl]penam

To a stirred slurry of 216 g. of 6-aminopenicillanic acid in 1,500 ml. of anhydrous chloroform in added 278 ml. of triethylamine. The mixture is stirred at ambient temperature until a clear solution is obtained (about 15 minutes) and is then cooled to about 0° C. Triphenylmethyl chloride (306 g.) is then added and stirring in continued at about 0° C. for 30 minutes, and then at ambient temperature for a further 24 hours. The mixture is then cooled to about 0° C., and 14 ml. of triethylamine, followed by 95 ml. of ethyl chloroformate, is added. During this process the temperature rises to about 15° C., and a precipitate forms. To facilitate stirring a further 200 ml. of chloroform is added. The stirring is continued for 30 minutes. Then, at about 0° C., 50 ml. of 4-methoxybenzylamine is injected into the reaction medium below the surface of the solvent. At 10 minute intervals, three further aliquots of 4-methoxybenzylamine (35 ml., 25 ml. and 21 ml.) are injected in the reaction in similar fashion. The total volume of 4-methoxybenzylamine added is 131 ml. The cooling bath is then removed, and the reaction mixture is stirred for one hour. The chloroform solution is washed successively with five 2,000-ml. portions of water and one 2,000-ml. portion of saturated brine. The chloroform is finally dried using anhydrous sodium sulfate.

Examination of the reaction mixture by NMR spectroscopy shows approximately 85% conversion of acid to amide. Accordingly, the chloroform solution is cooled in an ice-bath and 21 ml. of triethylamine, followed in about 5 minutes by 14.2 ml. of ethyl chloroformate, is added. After a further 15 minutes, 9.8 ml. of 4-methoxybenzylamine is added, and then in another 5 minutes a further 9.8 ml. of 4-methoxybenzylamine is added. The reaction is concentrated in vacuo giving 6-(triphenylmethylamino)-2,2-dimethyl-3-[N-(4-methoxybenzyl)carbamoyl]penam, as an amorphous solid.

EXAMPLE 2

6-(Triphenylmethylamino)-2,2-dimethyl-3-{chloro-[N-(4-methoxybenzyl)imino]methyl}penam The amide product of Example 1 is dissolved in 480 ml. of pyridine, and then the solution is cooled to about −5° C. To this solution is added dropwise, with stirring during 10 minutes, 108 ml. of thionyl chloride. The reaction mixture is then allowed to warm slowly to ambient temperature over a 21-hour period. All the volatile components are removed in vacuo leaving the crude imino chloride as an amorphous solid. The NMR spectrum (in CHCl$_3$) of this product shows absorption bands at 4.70 ppm (singlet, C-3hydrogen), 4.65 ppm (singlet, benzyl hydrogens), 4.30–4.60 ppm (multiplet, C-5 and C-6 hydrogens), 3.75 ppm (singlet, methoxy hydrogens), 1.57 ppm (singlet, C-2 methyl hydrogens) and 1.38 ppm (singlet, C-2 methyl hydrogens).

EXAMPLE 3

6-(Triphenylmethylamino)-2,2-dimethyl-3-[N'-(4-methoxybenzyl)amidino]penam

To a 0° C. solution of 13.1 g. (22 mmoles) of 6-(triphenylmethylamino)-2,2-dimethyl-3-{chloro-[N-(4-methoxybenzyl)imino]methyl{penam in 45 ml. of ethanol-free chloroform, a 1.33 N ammonia solution in chloroform is added all at once. The resulting mixture is stirred 5 minutes at 0° C. and then for 45 minutes at 25° C. The mixture is then filtered, and the filtrate rotoevaporated to an amber oil. Addition of ether (100 ml.) affords a precipitate which is filtered and then taken up in 150 ml. chloroform. The chloroform solution is washed first with 100 ml. 0.5N NaOH; and then with three 150 ml. portions of water. It is then dried over anhydrous sodium sulfate and rotoevaporated to afford the title compound as an orange foam. Rotoevaporation of the filtrate obtained after the ether precipitation procedure affords more of the title compound, as an orange foam. Total yield = 12.05 g. (95%). $^1$H-NMR (CDCl$_3$) ppm δ 1.33 (3H, s, 2-CH$_3$); 1.60 (3H, s, 2-CH$_3$); 1.60 (3H, S, 2-CH$_3$); 3.81 (3H, s, -OCH$_3$); 4.17– 4.68 (3H, m; 3-, 5- and 6-H); 4.24 (2H, s, —CH$_2$—), 4H, AB with H$_a$ within 7.2–7.68 multiplet; H$_b$ centered at 6.89, J = 9 HZ. (CH$_3$O—C$_6$-$_4$H—), 7.2—7.68 (15H, m, C$_6$H$_5$). Infrared (CH$_2$Cl$_2$) λmax (μ) 5.62 (s, strong); 5.75–5.83 (broad s, strong); 5.97 (broad s, strong).

EXAMPLE 4

6-(Triphenylmethylamino)-2,2-dimethyl-3-[1-(4-methoxybenzyl)-pyrimidin-4,6-dione-2-yl]penam To a stirred solution of 21.44 g. (104 mmoles) of N,N'-dicyclohexylcarbodiimide in 122 ml. of methylene chloride and 15 ml. dimethylformamide at −5° C., a solution of 29.9 g. (52 mmoles) of 6-(triphenylmethylamino)-2,2-dimethyl-3-[N'-(4-methoxybenzyl)amidino]penam and 5.41 g. (52 mmoles) of malonic acid in 122 ml. methylene chloride and 15 ml. dimethylformamide is added dropwise over 2 hours. The mixture is then stirred for 24 hours at 25° C. The N,N'-dicyclohexylurea precipitate (18.6 g., 79.8% of theory) is filtered off, and the filtrate washed with six 150 ml. portions of water. It is dried over anhydrous sodium sulfate and then rotoevaporated to yield the title compound in crude form as an orange foam (32.6 g.). The crude product is divided into two equal portions for silica gel chromatography (ethyl acetate elution) affording a total of 10.61 g. (31.6%) of the purified title compound. $^1$H-NMR (CDCl$_3$) ppm ($\delta$) 1.01 (3H, s, 2-CH$_3$); 1.44 (3H, s, 2CH$_3$); 3.80 (3H, s, —OCH$_3$); 4.31-4.73 (3H, m; 3-, 5- and 6H); 5.25 (2H, s, —CH$_2$—); 4H, AB, H$_a$ within a 7.18-7.68 multiplet, H$_b$ centered at 6.91, J = 8 Hz, CH$_3$O—C$_{6-4}$H—); 7.18-7.68 (15H, m, C$_{6-5}$H—).

EXAMPLE 5

The procedures of Examples 1-4 are repeated but using the appropriate substituted triphenylmethyl chloride reactant to provide the following compounds:

EXAMPLE 6

6-Ammonium-2,2-dimethyl-3-[1-(4-methoxybenzyl)-pyrimidin-4,6-dione-2-yl]penam Tosylate p-Toluenesulfonic acid monohydrate (2.32 g., 12.2 mmoles) is added to an acetone (133 ml.) solution of 10.32 g. (16 mmoles) of 6-(triphenylmethylamino)-2,2-dimethyl-3-[1-(4-methoxybenzyl)-pyrimidin-4,6-dione-2-yl]penam. The resulting solution is stirred for one hour at 25° C. The reaction mixture is then filtered and the filtrate rotoevaporated to a gum. Trituration of the gum with 150 ml. of ether affords the title compound as a pale yellow granular solid, which is isolated in quantitative yield by filtration and then dried in vacuo. $^1$H-NMR (DMSO) ppm ($\delta$) 1.24 (3H, s, 2-CH$_3$), 1.66 (3H, s, 2-CH$_3$); 2.31 (3H, s, C$_6$H$_5$—CH$_3$); 3.75 (3H, s, —OCH$_3$); 1H within multiplet 4.98-5.10 (d, J = 4Hz, 5-H); 5.10 (1H, s, 3-H); 5.55 (2H, s, —CH$_2$—); 5.85 (1H, d, J = 4Hz, 6-H).

In like manner the substituted triphenylmethyl derivatives of Example 5 are converted to the title compound.

EXAMPLE 7

6-Amino-2,2-dimethyl-3-[1-(4-methoxybenzyl)-pyrimi-

| R$_2$ | R$_3$ | R$_4$ | R$_2$ | R$_3$ | R$_4$ |
|---|---|---|---|---|---|
| 2-CH$_3$ | 2-CH$_3$ | H | H | H | 2-Br |
| H | H | 2-CH$_3$ | 4-Cl | 4-OCH$_3$ | H |
| 4-Cl | H | H | 3-OCH$_3$ | 3-OCH$_3$ | H |
| 4-Br | H | H | 4-OCH$_3$ | 4-OCH$_3$ | H |
| 4-F | H | H | 2-Br | 4-Br | 4-Br |
| 3-OCH$_3$ | H | H | 4-Cl | 4-Cl | 4-Cl |
| 4-OCH$_3$ | H | H | 4-CH$_3$ | 3-OCH$_3$ | 3-OCH$_3$ |
| 3-Cl | H | H | 3-OCH$_3$ | 3-OCH$_3$ | 3-OCH$_3$ |
| 2-F | H | H | 4-F | 4-F | 4-C$_6$H$_5$ |
| 4-CH$_3$ | H | H | 4-CH$_3$ | 4-CH$_3$ | 4-CH$_3$ |
| 4-n-C$_4$H$_9$ | H | H | 4-C$_6$H$_5$ | 4-C$_6$H$_5$ | 4-C$_6$H$_5$ |
| 3-O-n-C$_4$H$_9$ | H | H | 3-C$_6$H$_5$ | H | H |
| 2-OC$_2$H$_5$ | H | H | 3-CH$_3$ | H | H |
| 4-n-C$_3$H$_7$ | H | H | 3-F | H | H |
| 4-Cl | 4-Cl | H | 4-t-C$_4$H$_9$ | 4-t-C$_4$H$_9$ | 4-t-C$_4$H$_9$ |

Those substituted triphenylmethyl chlorides not described in the literature are prepared by reaction of the appropriate benzophenone with a Grignard reagent of an appropriately substituted bromobenzene, e.g., m-fluoro bromobenzene in the manner described in *J. Chem. Soc.*, 4257-62 (1957).

din-4,6-dione-2-yl]penam Acid Addition Salts

Repetition of the procedure of Example 6 but using the following acids in place of p-toluenesulfonic acid monohydrate affords acid addition salts wherein the acid corresponds to the acid used:
  benzene sulfonic acid
  methane sulfonic acid
  hydrogen chloride
  hydrogen bromide
  acetic acid
  trifluoroacetic acid nitric acid
β-naphthalene sulfonic acid
dichloroacetic acid
acetic acid
formic acid
benzoic acid

EXAMPLE 8

6-Ammonium-2,2-dimethyl-3-(pyrimidin-4,6-dione-2-yl)penam Tosylate

To 13 ml. of anhydrous hydrogen fluoride in a polyethylene vessel at −35° C., 7.85 g. (13.7 mmoles) of 6-ammonium-2,2-dimethyl-3-[1-(4-methoxybenzyl)-pyrimidin-4,6-dione-2-yl]penam tosylate is added all at once with rapid magnetic stirring. Vigorous stirring at −35° C. is continued for 35 minutes. Chilled (−10° C.) isopropyl ether (250 ml.) is then added to the solution to precipitate the title compound as a pale yellow granular solid. The product is washed on a filter with ether (three 10ml. portions) and dried in vacuo. Yield = 5.13 g. (78.8%). $^1$N-NMR (DMSO) ppm ($\delta$) 1.31 (3H, s, 2-CH$_3$); 1.69 (3H, s, 2-CH$_3$); 2.35 (3H, s, C$_6$H$_5$—CH$_3$); 5.12 (1H, d, J = 4Hz, 5-H), 5.39 (1H, s, 3-H); 5.75 (1H, d, J = 4Hz, 6-H); 7.00 and 7.53 (4H, AB, J = 8 Hz, CH$_3$-C$_6$-$_4$H). Infrared (KBr) λmax (μ) 5.60 (s, strong); 6.07 (s, strong). U.V. $\lambda_{max}^{DMSO}$ nm ($\epsilon$) 275 (ca. 4000).

The same product is obtained by substitution of 6-(triphenylmethylamino)-2,2-dimethyl-3-[1-(4-methoxybenzyl)pyrimidin-4,6-dione-2-yl]penam tosylate as reactant in the above procedure.

EXAMPLE 9

6-Amino-2,2-dimethyl-3-(pyrimidin-4,6-dione-2-yl)penam

The tosylate salt of Example 8 is converted to the free base form by neutralization with one equivalent of base such as sodium hydroxide, potassium hydroxide or triethylamine in water followed by freeze-drying of the aqueous mixture.

EXAMPLE 10

Acid Addition Salts of 6-Amino-2,2-dimethyl-3-(pyrimidin-4,6-dione-2-yl)penam

To 6-amino-2,2-dimethyl-3-(pyrimidin-4,6-dione-2-yl)penam is water is added an equimolar amount of the appropriate acid. The mixture is stirred for one hour and then freeze-dried to give the acid addition salt. In this manner the following salts are prepared:
hydrochloride
sulfate
hydrobromide
benzoate
acetate
propionate
benzenesulfonate
α-naphthalenesulfonate
β-naphthalenesulfonate
methane sulfonate
malate
citrate
gluconate
glycolate
tartrate

EXAMPLE 11

6-Phenylacetamido-2,2-dimethyl-3-(pyrimidin-4,6-dione-2yl)penam

To a −5° C. solution of 4.57 g. (10.1 mmoles) of 6-ammonium-2,2-dimethyl-3-(pyrimidin-4,6-dione-2-yl)penam tosylate and 3.01 ml. (26.9 mmoles) N-methylmorpholine in 200 ml. of anhydrous methylene chloride, a solution consisting of 1.47 ml. (10.1 mmoles) phenylacetyl chloride in 20 ml. anhydrous methylene chloride in added dropwise over a 10-minute period. The mixture is allowed to warm to 25° C. and stirred at that temperature for 2 hours. It is washed with 300 ml. of water; and then layered with a fresh 250 ml. of water. The pH of the aqueous phase is adjusted to 2.5 with 6N hydrochloric acid. The organic phase is separated, washed with 300 ml. of water, dried over sodium sulfate, and rotoevaporated to afford the title compound as a yellow foam. Yield = 3.22 g. (79.9%). $^1$H-NMR (DMSO) ppm ($\delta$) 1.30 (3H, s, 2-CH$_3$); 1.67 (3H, s, 2-CH$_3$); 3.62 (2H, s, —CH$_2$—); 4.74 (1H, s, 3-H); 5.32–5.82 (2H within multiplet, 5- and 6-H); 7.83 (5H, s, —C$_6$-$_5$H). Infrared (KBr) λmax (μ) 5.60 (s, strong), 6.07 (s, strong).

EXAMPLE 12

6-Phenoxyacetamido-2,2-dimethyl-3-(pyrimidin-4,6-dione-2-yl)penam

The title compound is prepared in a manner analogous to that described for preparation of 6-(phenylacetamido)-2,2-dimethyl-3-(pyrimidin-4,6-dione-2-yl)penam, but using phenoxyacetyl chloride in place of phenylacetyl chloride.

EXAMPLE 13

6-(D-2-Azido-2-phenylacetamido)-2,2-dimethyl-3-(pyrimidin-4,6-dione-2-yl)penam

A solution of 1.77 g. (0.01 mole) of D-2-azido-2-phenylacetic acid and 5 ml. of thionyl chloride is heated under reflux for one hour. Rotoevaporation of the solvent affords a residue of D-2-azido-2-phenylacetyl chloride. The residue is dissolved in 10 ml. of methylene chloride and the resulting solution added over 5 minutes to a 0° C. solution of 4.22 g. (0.01 mole) of 6-ammonium-2,2-dimethyl-3-(pyrimidin-4,6-dione-2-yl)penam tosylate and 3.33 ml. (0.03 mole) of N-methylmorpholine in 50 ml. of anhydrous methylene chloride. After 30 minutes at 0° C., the reaction mixture is allowed to warm to 25° C. It is stirred for 2 hours at 25° C., and is then diluted with 100 ml. methylene chloride. It is then washed with three 200 ml. portions of dilute aqueous hydrochloric acid (pH 2), then with three 200 ml. portions of water, and is then dried over anhydrous sodium sulfate. The title compound is isolated by evaporation of the solvent under reduced pressure.

EXAMPLE 14

6-(D-2-amino-2-phenylacetamido)-2,2-dimethyl-3-(pyrimidin-4,6-dione-2-yl)penam

To a solution of 4.25 g. (0.01 mole) of 6-(D-2-azido-2-phenylacetamido)-2,2-dimethyl-3-(pyrimidin-4,6-dione-2-yl)penam in 100 ml. of methanol and 10 ml. of a normal aqueous solution of acetic acid is added 3 g. of 5% palladium-on-carbon. The mixture is then shaken under a pressure of 2 atmospheres of hydrogen until the theoretical amount of hydrogen is consumed. The catalyst is then removed by filtration and washed with water-methanol (1:1). The combined filtrate and wash solutions are concentrated under reduced pressure to remove the methanol. The aqueous solution is acidified to pH 3 with hydrochloric acid and extracted twice with 10 ml. volumes of butyl acetate and once with 10 ml. of ether. Lyophilization of the aqueous solution, after neutralization with sodium hydroxide, affords the sodium salt of the title compound.

What is claimed is:

1. A compound having the formula

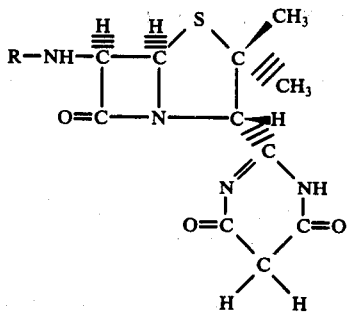

wherein R is selected from the group consisting of 2-phenylacetyl, 2-phenoxyacetyl, 2-azido-2-phenylacetyl and 2-amino-2-phenylacetyl.

2. The compound of claim 1 wherein R is 2-amino-2-phenylacetyl.

3. The compound of claim 1 wherein R is 2-phenylacetyl.

4. The compound of claim 1 wherein R is 2-phenoxylacetyl.

5. The compound of claim 1 wherein R is 2-azido-2-phenylacetyl.

* * * * *